(12) United States Patent
Jinno et al.

(10) Patent No.: US 8,002,784 B2
(45) Date of Patent: Aug. 23, 2011

(54) MANIPULATOR

(75) Inventors: Makoto Jinno, Ota-ku (JP); Takamitsu Sunaoshi, Yokohama (JP); Shigeru Omori, Ashigarakami-gun (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 268 days.

(21) Appl. No.: 11/743,222

(22) Filed: May 2, 2007

(65) Prior Publication Data
US 2007/0288044 A1 Dec. 13, 2007

(30) Foreign Application Priority Data
May 12, 2006 (JP) ................. 2006-133973

(51) Int. Cl.
*A61B 17/32* (2006.01)
(52) U.S. Cl. ............. 606/174; 606/208; 81/381
(58) Field of Classification Search .......... 606/139, 606/142, 149, 170, 167, 174, 205, 206, 207, 606/208, 51, 52; 414/729, 739, 740; 294/104, 294/116, 101, 95, 96; 901/30, 31, 36, 39, 901/32; 81/381
See application file for complete search history.

(56) References Cited

U.S. PATENT DOCUMENTS

| | | | | |
|---|---|---|---|---|
| 576,179 A | * | 2/1897 | Wood | 72/422 |
| 1,733,547 A | * | 10/1929 | Lorenz | 414/626 |
| 1,874,944 A | * | 8/1932 | Fabian | 81/426 |
| 3,212,651 A | * | 10/1965 | Specht et al. | 414/7 |
| 4,367,998 A | * | 1/1983 | Causer | 414/4 |
| 4,473,249 A | * | 9/1984 | Valentine et al. | 294/88 |
| 5,033,785 A | * | 7/1991 | Woolley, Jr. | 294/104 |
| 5,392,789 A | * | 2/1995 | Slater et al. | 600/564 |
| 5,423,854 A | | 6/1995 | Martin et al. | |
| 6,889,116 B2 | | 5/2005 | Jinno | |
| 2001/0044635 A1 | * | 11/2001 | Niizeki et al. | 606/205 |
| 2004/0176751 A1 | | 9/2004 | Weitzner et al. | |
| 2005/0033358 A1 | * | 2/2005 | Suzuki | 606/207 |
| 2005/0119693 A1 | * | 6/2005 | Prestel | 606/207 |
| 2006/0087138 A1 | * | 4/2006 | Migliori | 294/104 |

FOREIGN PATENT DOCUMENTS

| | | |
|---|---|---|
| EP | 1 481 643 A1 | 12/2004 |
| JP | 2002-102248 | 4/2002 |
| JP | 2003-61969 | 3/2003 |

* cited by examiner

*Primary Examiner* — Anhtuan T Nguyen
*Assistant Examiner* — David Eastwood
(74) *Attorney, Agent, or Firm* — Oblon, Spivak, McClelland, Maier & Neustadt, L.L.P.

(57) ABSTRACT

A manipulator has a working unit in which when at least a first end effector finger and a second end effector finger are maximally closed on each other, at least the distance between a third joint axis and a first joint axis is greater than the distance between the first joint axis and a distal end of the second end effector finger, or the distance between the third joint axis and the first joint axis is greater than the distance between third joint axis and a second joint axis, or the angle formed between a direction from the third joint axis to the first joint axis and a direction from the third joint axis to the second joint axis is not π.

9 Claims, 13 Drawing Sheets

MANIPULATOR

BACKGROUND OF THE INVENTION

1. Field of the Invention

The present invention relates to a manipulator for actuating a working unit by operating an operating unit.

2. Description of the Related Art

Heretofore, there has been used in the art an integral medical manipulator having an end working unit and a hand-operating unit which are connected to each other by a connector. Under endoscopic observation, the hand-operating unit is held by hand and operated to insert the end working unit into a body cavity and then actuate the end working unit to perform various medical treatments on the living body tissue.

Japanese Laid-Open Patent Publication No. 2003-61969 discloses a manipulator having an operating unit and a working unit which incorporates in the operating unit a pair of grippers for gripping a living body tissue. The grippers can be opened and closed about a gripper shaft, and can be angularly movable in unison about a pitch axis and a roll axis. A wire is trained around the output shaft of a motor housed in the operating unit and a pulley housed in the working unit through a connector. The torque that is required to operate the working unit is transmitted from the motor through the wire to the pulley, and then from the pulley to gears.

A manipulator disclosed in Japanese Laid-Open Patent Publication No. 2002-102248 is similar in structure to the manipulator disclosed in Japanese Laid-Open Patent Publication No. 2003-61969, and further includes a power boosting mechanism disposed in the working unit for increasing the gripping forces of the grippers.

With the manipulator disclosed in Japanese Laid-Open Patent Publication No. 2003-61969, it is difficult to increase the gripping forces of the grippers. For example, if the output torque of the motor is simply increased to increase the gripping forces, then the expansion and contraction properties and tensile strength of the wire, and the mechanical strength of the torque transmitting mechanism have to be increased. However, these efforts make it difficult to reduce the diameter of the connector. In addition, since various components for achieving movements about the respective axes need to be installed in the working unit which is of a small size, they pose a spatial limitation on attempts to increase the speed reduction ratio in the working unit.

Although the gripping forces of the grippers are increased by the power boosting mechanism in the manipulator disclosed in Japanese Laid-Open Patent Publication No. 2002-102248, the grippers are offset with respect to each other when they grip a living body tissue. Therefore, the operator is required to operate the manipulator while at the same time predicting a vertical offset action of the grippers. For this reason, there have been demands from manipulator operators (e.g., surgeons) for a manipulator that can be operated neatly and smoothly without the need for a burden in predicting the offset action.

SUMMARY OF THE INVENTION

It is an object of the present invention to provide a manipulator which is capable of generating large gripping forces and which produces a small offset action when gripping a living body tissue.

A manipulator according to an aspect of the present invention includes a first end effector extending from one end to another end, the first end effector having a first end effector portion on the end, a first link on the other end, and a first joint disposed between the first end effector finger and the first link, a second end effector extending from an end to another end, the second end effector having a second end effector portion on the end, a second link on the other end, and a second joint disposed between the second end effector finger and the second link, a link bar extending from one end to another end, a first junction connecting the second joint to the first joint such that the second end effector has a longitudinal direction substantially perpendicular to a first joint axis which extends through the first junction substantially perpendicularly to a longitudinal direction of the first end effector, and the second end effector is angularly movable about the first joint axis with respect to the first end effector, a second junction connecting the other end of the link bar to another end of the first link such that the link bar has a longitudinal direction substantially perpendicular to a second joint axis which extends through the other end of the first link substantially perpendicularly to a longitudinal direction of the first link, and the link bar is angularly movable about the second joint axis with respect to the first link, and a third junction connecting the one end of the link bar to another end of the second link such that the second link has a longitudinal direction substantially perpendicular to a third joint axis which extends through the one end of the link bar substantially perpendicularly to the longitudinal direction of the link bar, the link bar is angularly movable about the third joint axis with respect to the second link, and the one end of the link bar is movable in the longitudinal direction of the second link with respect to the second link.

According to the present invention, the manipulator is capable of generating increased gripping forces and makes a small offset action when it grips a living body tissue.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Manipulators according to various embodiments of the present invention will be described in detail below with reference to the drawings.

In the description of the embodiments of the present invention, it is assumed that a working unit side of a manipulator is a distal end side, and directions which refer to distal and proximal ends of the manipulator mean relative directions based on the assumption. The term "theoretically" used in the description refers to an ideal state wherein disturbance factors such as dimensional errors of parts, play of sliding parts, and deformations of parts which are not detrimental to the operation of the manipulator are not taken into account. Actual manipulators are subject to elements (e.g., an offset action, frictional resistance, etc.) due to such disturbance factors.

1st Embodiment

A manipulator according to a first embodiment of the present invention will be described below with reference to FIGS. 1 through 7B.

Figure 1:
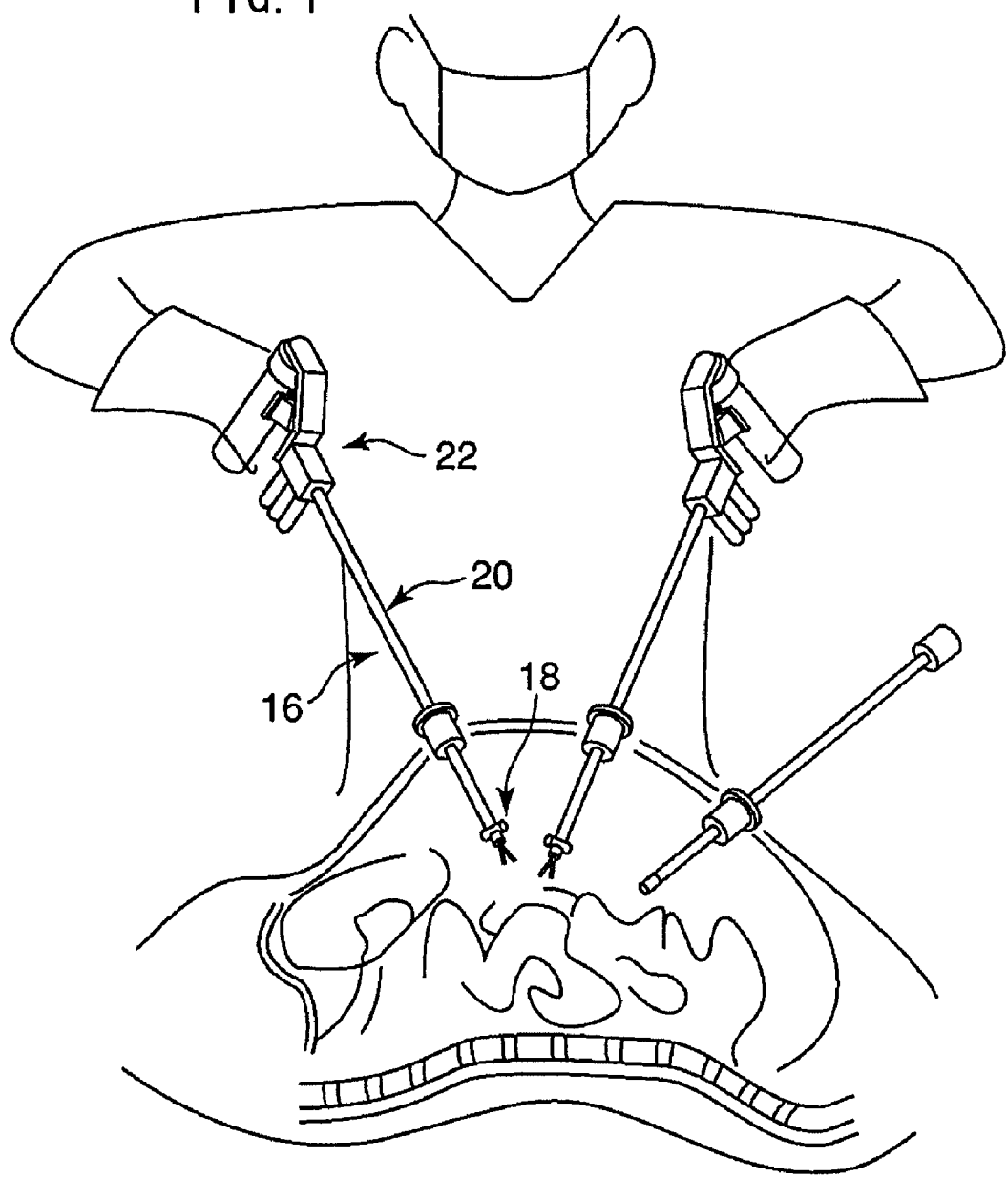
FIG. 1 is a perspective view of a manipulator according to a first embodiment of the present invention.

As shown in FIG. 1, a manipulator 16 according to the first embodiment of the present invention is a clip applier for applying clips. The manipulator 16 generally comprises a working unit 18 for medically treating or applying clips to a living body tissue, a slender connecting shaft 20, an operating unit 22 which is held and operated by the operator for actuating the working unit 18. The working unit 18, the connecting shaft 20, and the operating unit 22 are positioned successively from the distal end side of the manipulator 16.

Figure 2:
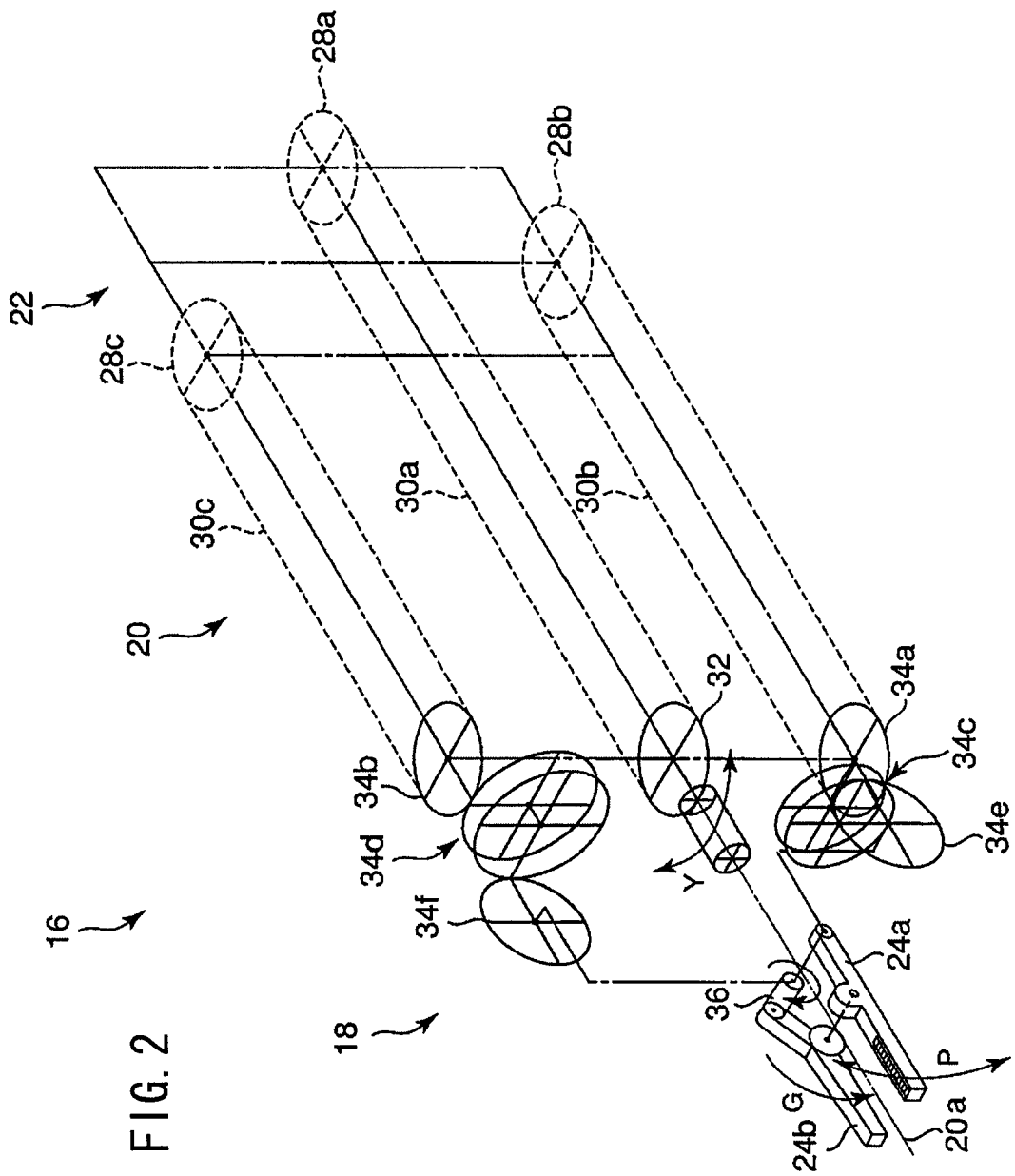
FIG. 2 is a schematic perspective view of a drive mechanism of the manipulator according to the first embodiment of the present invention.
Figure 3:
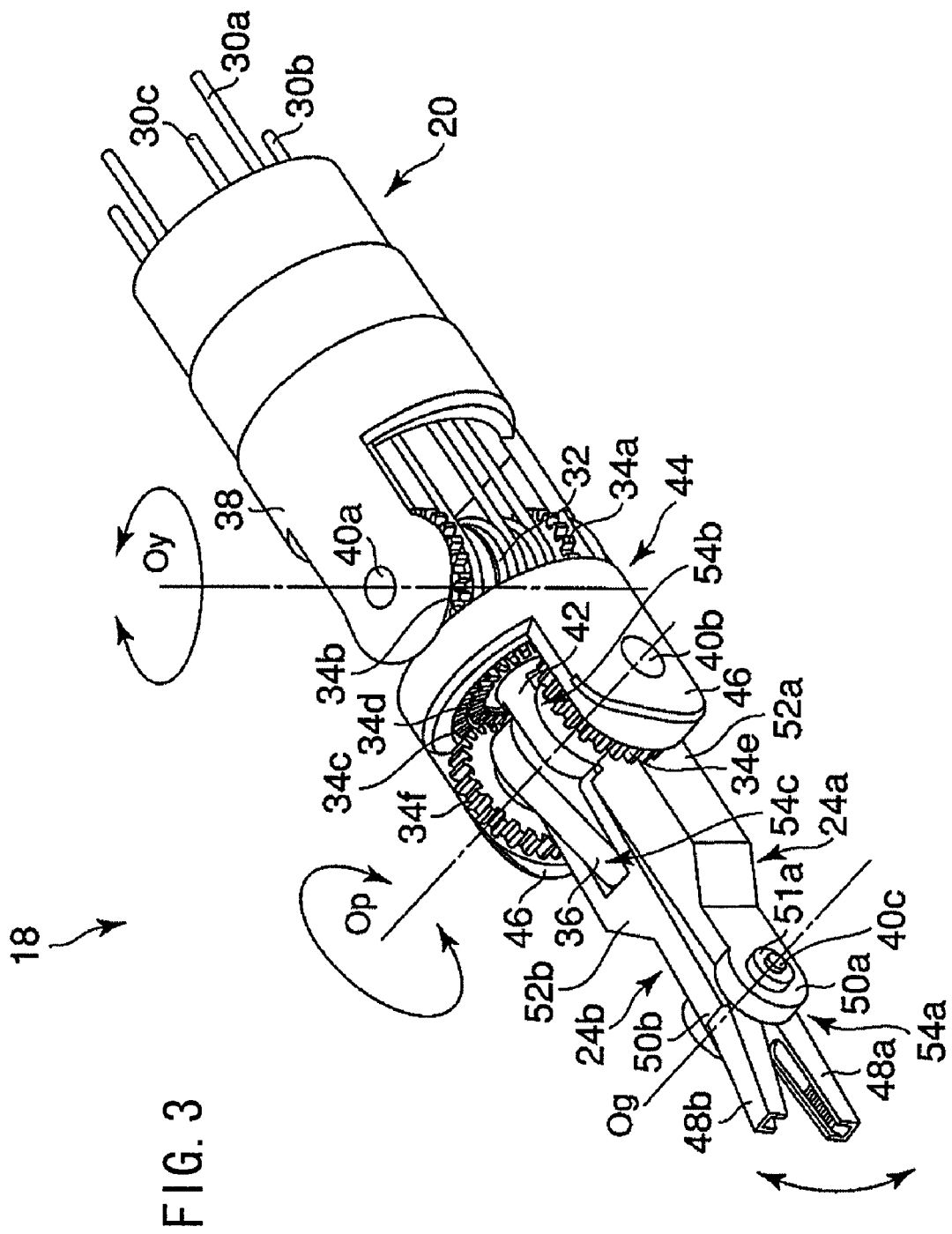
FIG. 3 is a perspective view of a working unit of the manipulator according to the first embodiment of the present invention.
Figure 4:
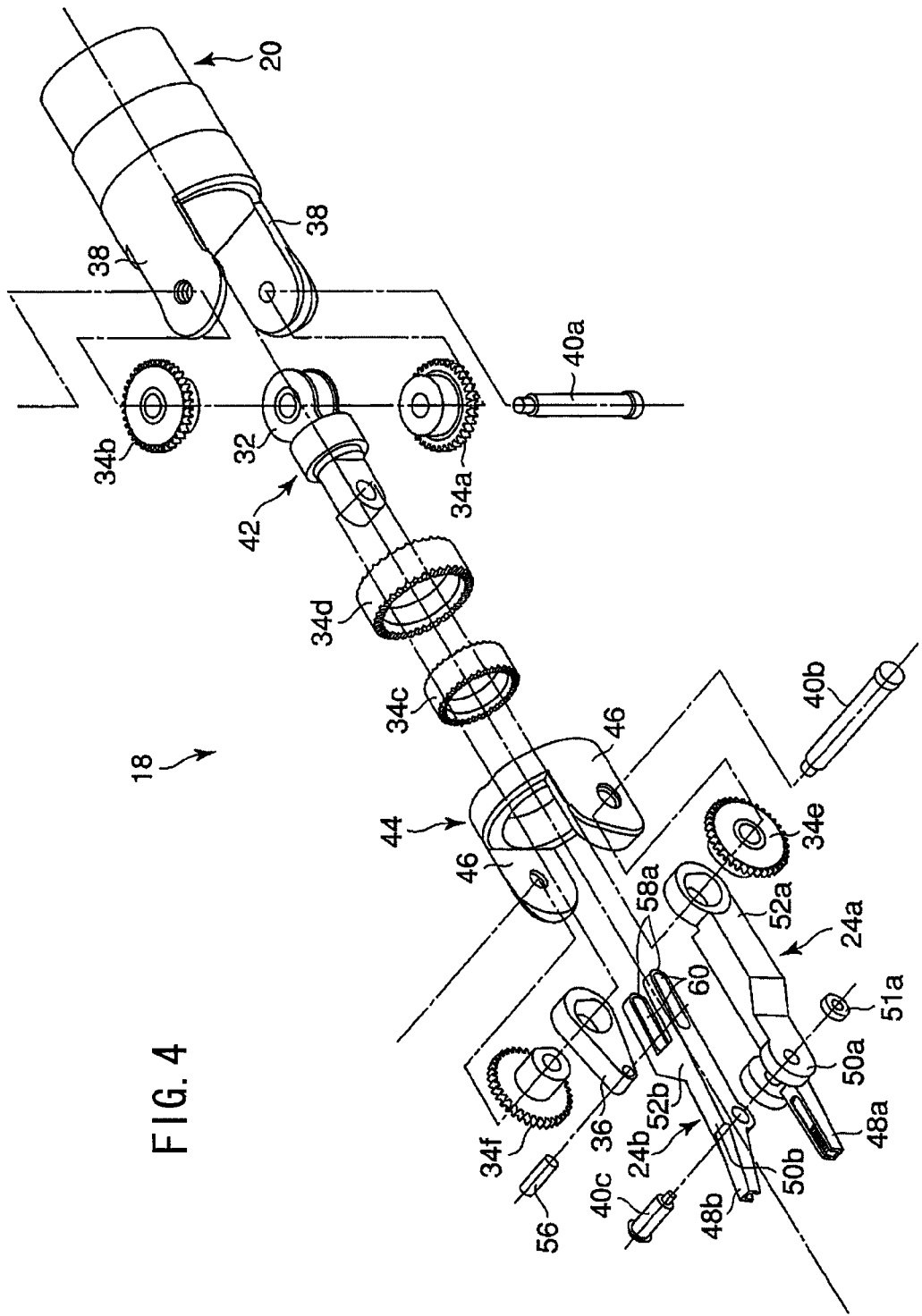
FIG. 4 is an exploded perspective view of the working unit of the manipulator according to the first embodiment of the present invention.
Figure 5A:
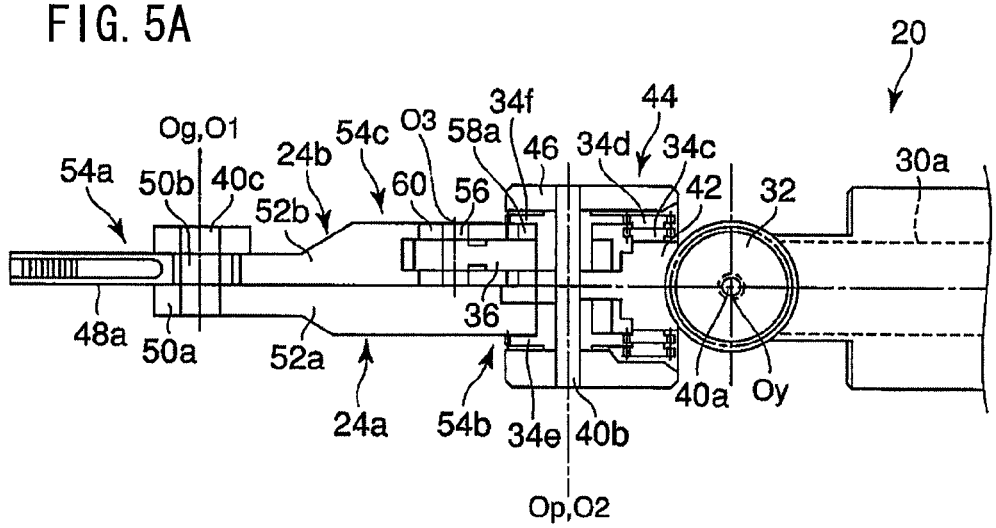
FIG. 5A is a plan view of the working unit of the manipulator according to the first embodiment of the present invention.
Figure 5B:
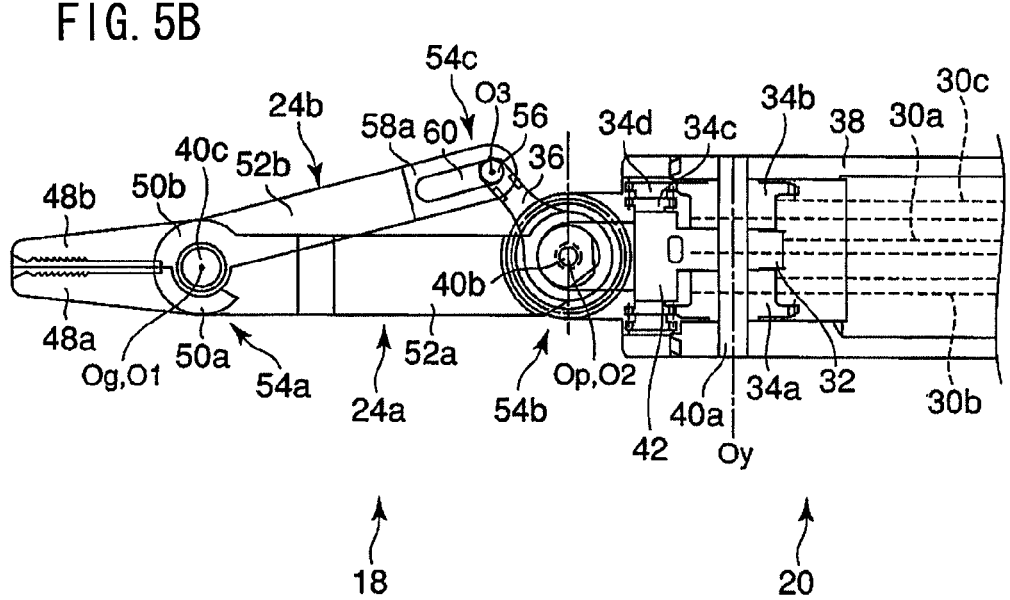
FIG. 5B is a side elevational view of the working unit of the manipulator according to the first embodiment of the present invention.

As shown in FIG. 2, the working unit 18 has a pair of first and second end effectors 24a, 24b angularly movable in the directions indicated by the arrow Y about a yaw axis which extends substantially perpendicularly to a main axis 20a of the working unit 18. The working unit 18 has a pulley 32 disposed therein, and the operating unit 22 has a first motor output shaft 28a disposed therein. A first wire 30a is trained around the pulley 32 and the first motor output shaft 28a and extends inside the connecting shaft 20. A torque for angularly moving the first and second end effectors 24a, 24b about the yaw axis is transmitted from the first motor output shaft 28a through the first wire 30a and the pulley 32 to the first and second end effectors 24a, 24b.

The first and second end effectors 24a, 24b are also angularly movable in the directions indicated by the arrow P about a pitch axis which extends substantially perpendicularly to the main axis 20a and the yaw axis. The working unit 18 has an intermeshing set of first, third, and fifth gears 34a, 34c, 34e disposed therein, and the operating unit 22 has a second motor output shaft 28b disposed therein. A second wire 30b is trained around the first gear 34a and the second motor output shaft 28b and extends inside the connecting shaft 20. A torque for angularly moving the first and second end effectors 24a, 24b about the pitch axis is transmitted from the second motor output shaft 28b through the second wire 30b and the first, third, and fifth gears 34a, 34c, 34e to the first and second end effectors 24a, 24b.

The second end effector 24b is also angularly movable toward and away from, i.e., openable away from and closable on the first end effector 24a in the directions indicated by the arrow G about a gripper axis which extends substantially parallel to the pitch axis. The working unit 18 has an intermeshing set of second, fourth, and sixth gears 34b, 34d, 34f disposed therein, and the operating unit 22 has a third motor output shaft 28c disposed therein. A third wire 30c is trained around the second gear 34b and the third motor output shaft 28c and extends inside the connecting shaft 20. A torque for angularly moving the second end effector 24b about the gripper axis is transmitted from the third motor output shaft 28c through the third wire 30c and the second, fourth, and sixth gears 34b, 34d, 34f and the link bar 36 to the first and second end effectors 24a, 24b.

The working unit 18 of the manipulator 16 according to the first embodiment will be described in detail below with reference to FIGS. 3 through 7B.

As shown in FIGS. 3 through 5B, the connecting shaft 20 has a pair of diametrically opposite tongues 38 projecting toward the distal end thereof and disposed in facing relation to the central axis of the connecting shaft 20. The tongues 38 have respective engaging holes defined therein which receive therein the respective opposite ends of a first turn shaft 40a. The first turn shaft 40a extends substantially perpendicularly to the central axis of the connecting shaft 20. The first turn shaft 40a has a central axis serving as a yaw axis Oy.

The pulley 32 which is mounted on the proximal end of a main shaft 42 is rotatably fitted over the first turn shaft 40a. When the pulley 32 is angularly moved around the first turn shaft 40a by the first wire 30a trained therearound, the main shaft 42 is turned around the first turn shaft 40a.

First and second gears 34a, 34b, which are hollow, substantially cylindrical in shape, are rotatably fitted over the first turn shaft 40a, one on each side of the pulley 32. Each of the first and second gears 34a, 34b has a shaft on an inner end thereof and a toothed member on an outer end thereof which has a number of successive gear teeth on an entire outer circumferential surface thereof. The second and third wires 30b, 30c are trained respectively around the shafts of the first and second gears 34a, 34b. The first and second gears 34a, 34b can be rotated about the axis of the first turn shaft 40a by the respective second and third wires 30b, 30c. The wires 30a, 30b, 30c are trained around the respective pulley and shafts by 1.5 turns and have portions fixed to the respective pulley and shafts.

The third gear 34c, which is of a ring shape, is rotatably mounted on an intermediate cylindrical portion of the main shaft 42 for rotation about the axis of the main shaft 42. The fourth gear 34d, which is of a ring shape, is rotatably mounted on the third gear 34c for rotation about the axis of the main shaft 42. Each of the third and fourth gears 34c, 34d has toothed distal and proximal end faces each having a number of successive gear teeth on an entire circumferential surface thereof. The gear teeth of the first gear 34a are held in mesh with the gear teeth on the proximal end of the third gear 34c, so that the third gear 34c can be rotated by the first gear 34a. The gear teeth of the second gear 34b are held in mesh with the gear teeth on the proximal end of the fourth gear 34d, so that the fourth gear 34d can be rotated by the second gear 34b. A cover 44 has a hollow cylindrical portion on its proximal end which is fitted over the fourth gear 34d. The fourth gear 34d is rotatable with respect to the hollow cylindrical portion of the cover 44 for rotation about the axis of the main shaft 42. The proximal end of the cover 44 is rollingly held against distal end faces of the pair of tongues 38 of the connecting shaft 20 for rolling movement around the first turn shaft 40a through a second turn shaft 40b.

When the pulley 32 is rotated by the first wire 30a, the third gear 34c, the fourth gear 34d, and the cover 44 are angularly moved in unison with the main shaft 42 around the first turn shaft 40a, i.e., the yaw axis Oy.

The cover 44 also has a pair of diametrically opposite lobes 46 extending from the distal end of the hollow cylindrical portion thereof and disposed in facing relation to each other across the central axis of the connecting shaft 20. The main shaft 42 has a distal end portion disposed between and parallel to the lobes 46. The second turn shaft 40b extends through a through hole defined in the distal end of the main shaft 42 and has opposite ends engaging in respective engaging holes defined in the respective lobes 46. The second turn shaft 40b lies substantially perpendicularly to the main axis 20a and the yaw axis Oy, and has a central axis serving as a pitch axis Op.

The fifth gear 34e, which is of a substantially tubular shape, is rotatably mounted on the second turn shaft 40b and disposed on one side of the main shaft 42 between the lobes 46 of the cover 44. The fifth gear 34e has a shaft on an inner end thereof and a toothed member on an outer end thereof which has a number of successive gear teeth on an entire outer circumferential surface thereof. The gear teeth of the fifth gear 34e are held in mesh with the gear teeth on the distal end of the third gear 34c, so that the fifth gear 34e can be rotated by the third gear 34c. The shaft of the fifth gear 34e has an asymmetric cross-sectional shape perpendicular to the axis thereof, and is nonrotatably inserted in an engagement hole defined in the proximal end of the first end effector 24a. When the first gear 34a is rotated by the second wire 30b, the third and fifth gears 34c, 34e are rotated to angularly move the first end effector 24a, together with the second end effector 24b, around the second turn shaft 40b, i.e., the pitch axis Op.

The first and second end effectors 24a, 24b have respective first and second end effector fingers (portions) 48a, 48b, respective first and second joints 50a, 50b, and respective first and second links 52a, 52b, which are arranged successively from their distal ends. The second joint 50b of the second end effector 24b is pivotally coupled to the first joint 50a of the first end effector 24a by a third turn shaft 40c and a fastening nut 51a, thereby making up a first junction 54a. The third turn shaft 40c extends substantially parallel to the pitch axis Op and has a central axis serving as a gripper axis Og. The third turn shaft 40c extends substantially perpendicularly to the longitudinal axes of the first and second end effectors 24a, 24b. The gripper axis Og, which is provided as the central axis of the third turn shaft 40c, will also be referred to as a first joint axis O1.

The second end effector 24b is angularly movable about the first joint axis O1 with respect to the first end effector 24a. A clip can be placed between the first and second end effector fingers 48a, 48b, and can be crimped by the first and second end effector fingers 48a, 48b when they are closed. The second end effector finger 48b is disposed in facing relation to the first end effector finger 48a across a gripping reference plane formed by the direction of the first joint axis O1 and the longitudinal axis of the first end effector finger 48a, and can be angularly moved on one side of the gripping reference plane. The second link 52b is offset from the first link 52a along the first joint axis O1, and can be angularly moved across the gripping reference plane.

The sixth gear 34f, which is similar in structure to the fifth gear 34e, is rotatably mounted on the second turn shaft 40b and disposed on the other side of the main shaft 42 between the lobes 46 of the cover 44. The gear teeth of the sixth gear 34f are held in mesh with the gear teeth on the distal end of the fourth gear 34d, so that the sixth gear 34f can be rotated by the fourth gear 34d. The shaft of the sixth gear 34f is nonrotatably inserted in an engagement hole defined in the proximal end of a link bar 36. The proximal end of the link bar 36 is thus pivotally mounted on the proximal end of the first end effector 24a by the sixth gear 34f, the second turn shaft 40b, and the fourth gear 34d, thereby making up a second junction 54b. The second turn shaft 40b extends substantially parallel to the longitudinal axes of the first link 52a and the link bar 36. The pitch axis Op, which is provided as the central axis of the second turn shaft 40b, will also be referred to as a second joint axis O2.

A slide pin 56 that is rotatable about its own axis is inserted in a through hole defined in the distal end of the link bar 36 substantially parallel to the first and second joint axes O1, O2. The proximal end of the second link 52b of the second end effector 24b has a pair of fork ends (portions) 58a disposed parallel to each other along the second joint axis O2 and extending in the longitudinal direction of the second link 52b. The fork ends 58a have respective slots 60 defined therein which extend in the longitudinal direction of the second link 52b. The distal end portion of the link bar 36 is disposed between the fork ends 58a of the second link 52b. The slide pin 56 that extends through the link bar 36 is inserted in the slots 60 for sliding movement therein in the longitudinal direction of the second link 52b. In other words, the distal end portion of the link bar 36 is pivotally mounted on the proximal end portion of the second link 52b for sliding movement in the longitudinal direction of the second link 52b, thereby making up a third junction 54c. The slide pin 56 has a central axis extending substantially perpendicularly to the longitudinal axes of the link bar 36 and the second link 52b. The central axis of the slide pin 56 will also be referred to as a third joint axis O3. The distal end portion of the link bar 36 is angularly movable, together with the second link 52b, across the gripping reference plane.

Figure 6A:
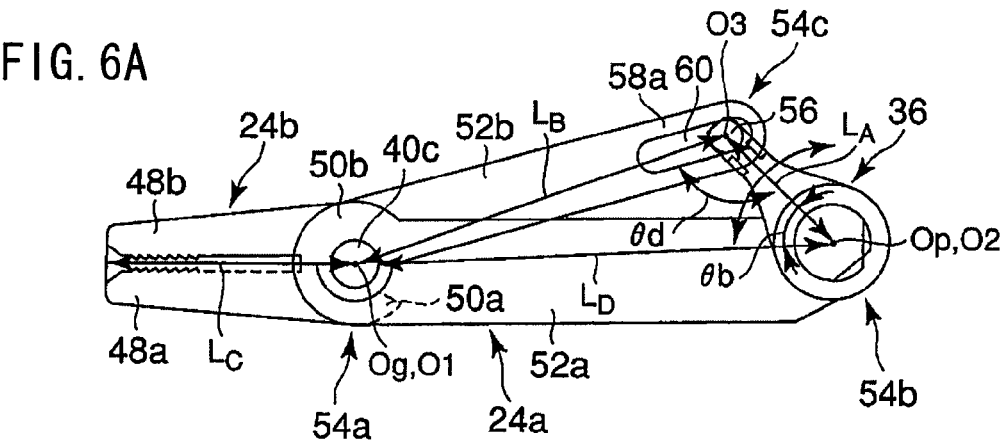
FIG. 6A is a side elevational view of the working unit of the manipulator according to the first embodiment of the present invention, the view showing a state in which first and second end effectors of the working unit are maximally closed on each other.
Figure 6B:
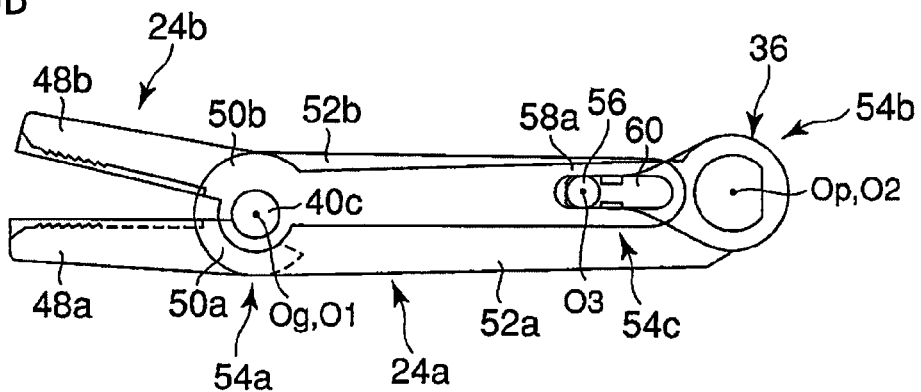
FIG. 6B is a side elevational view of the working unit of the manipulator according to the first embodiment of the present invention, the view showing a state in which the first and second end effectors of the working unit are in an intermediate position in their opening and closing operation.
Figure 6C:
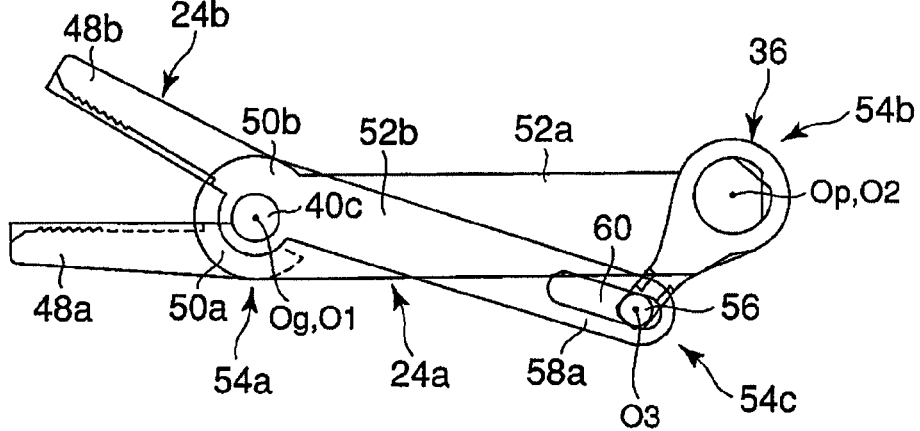
FIG. 6C is a side elevational view of the working unit of the manipulator according to the first embodiment of the present invention, the view showing a state in which the first and second end effectors of the working unit are maximally opened away from each other.

As shown in FIGS. 6A through 6C, the second end effector finger 48b is openable away from and closable on the first end effector finger 48a on one side of the gripping reference plane. When the distal end portion of the link bar 36 is turned to one side of the gripping reference plane, and the slide pin 56 in the distal end of the link bar 36 is held against the proximal end of the slots 60, or when the second end effector finger 48b is held against the first end effector finger 48a, the second end effector finger 48b is maximally closed on the first end effector finger 48a (see FIG. 6A). When the distal end portion of the link bar 36 is turned from one side of the gripping reference plane to the other side thereof across the gripping reference plane, and the slide pin 56 in the distal end of the link bar 36 is held against the proximal end of the slots 60, the second end effector finger 48b is maximally opened away from the first end effector finger 48a (see FIG. 6C). Thus, the slide pin 56 and the slots 60, or the slide pin 56, the slots 60, and the first and second end effector fingers 48a, 48b jointly make up a mechanical stopper for limiting a maximum open angle and a maximum closed angle between the first and second end effector fingers 48a, 48b.

Figure 7A:
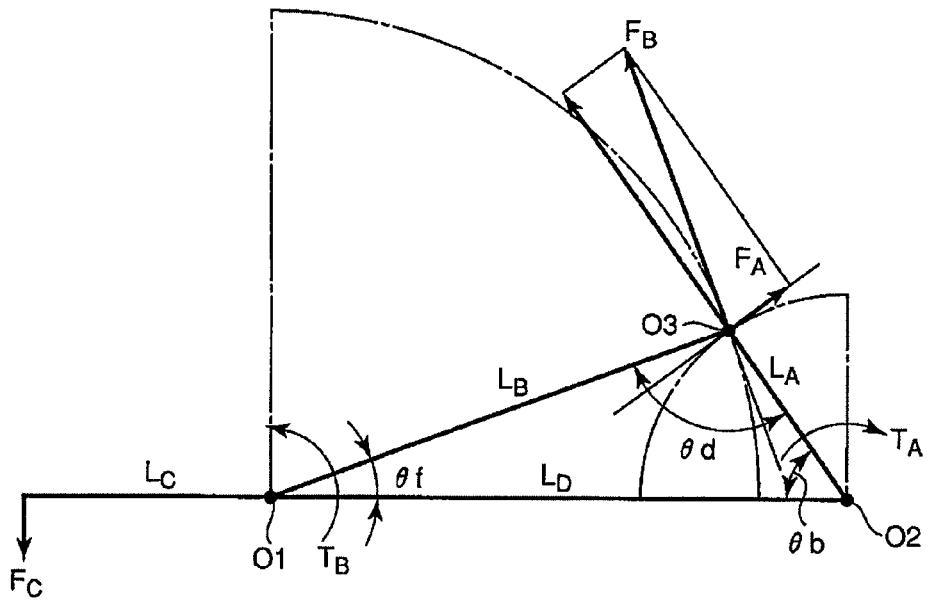
FIG. 7A is a diagram illustrative of a power boosting mechanism of the manipulator according to the first embodiment of the present invention, the view showing a state in which the first and second end effectors of the working unit are maximally closed on each other.
Figure 7B:
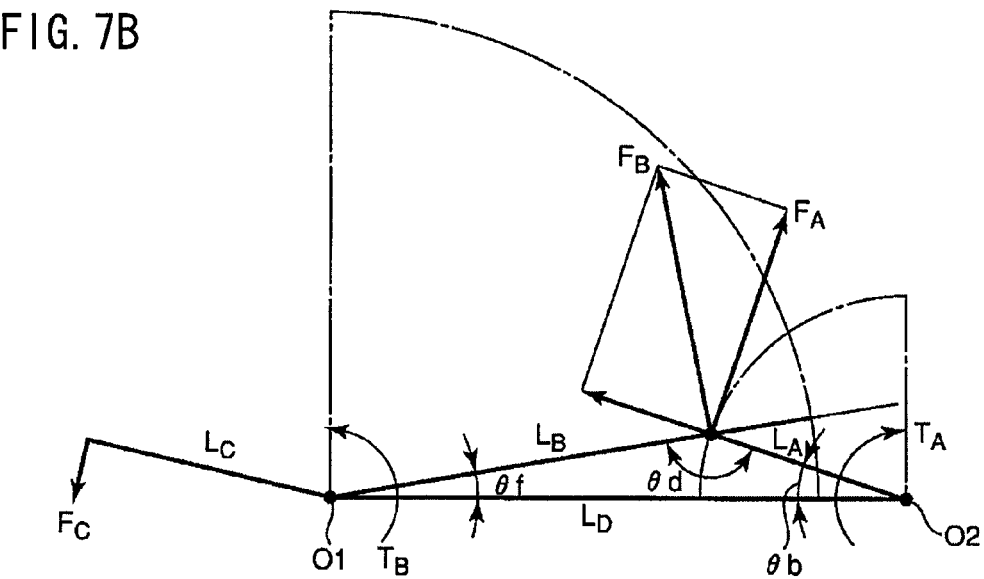
FIG. 7B is a diagram illustrative of the power boosting mechanism of the manipulator according to the first embodiment of the present invention, the view showing a state before the first and second end effectors of the working unit are maximally closed on each other.

A power boosting mechanism for increasing the gripping forces of the first and second end effector fingers 48a, 48b will be described below with reference to FIGS. 7A and 7B.

Various distances, angles, torques, and forces are defined as follows:

$L_A$: the longitudinal length of the link bar 36 (the distance between the second joint axis O2 and the third joint axis O3);

$L_B$: the distance between the first joint axis O1 and the third joint axis O3 (corresponding to the longitudinal length of the second link 52b when the first and second end effector fingers 48a, 48b are maximally opened away from each other);

$L_C$: the longitudinal length of the second end effector finger 48b (the distance between the first joint axis O1 and the distal end of the second end effector 24b);

$L_D$: the longitudinal length of the first link 52a (the distance between the first joint axis O1 and the second joint axis O2);

$\theta_b$: the angle formed between the first link 52a and the link bar 36 (the angle formed between a direction from the second joint axis O2 to the first joint axis O1 and a direction from the second joint axis O2 to the third joint axis O3);

$\theta_d$: the angle formed between the link bar 36 and the second link 52b (the angle formed between a direction from the third joint axis O3 to the first joint axis O1 and a direction from the third joint axis O3 to the second joint axis O2);

$\theta_f$: the angle formed between the first link 52a and the second link 52b (the angle formed between a direction from the first joint axis O1 to the second joint axis O2 and a direction from the first joint axis O1 to the third joint axis O3);

$T_A$: the torque applied to the proximal end of the link bar 36 around the second joint axis O2 (the direction indicated by the arrow is positive);

$T_B$: the torque applied to the proximal end of the second end effector finger 48b around the first joint axis O1 (the direction indicated by the arrow in the drawings is positive);

$F_A$: the force acting on the distal end of the link bar 36 perpendicularly to the longitudinal direction of the link bar 36 (the direction indicated by the arrow in the drawings is positive);

$F_B$: the force acting on the proximal end of the second link 52b perpendicularly to the longitudinal direction of the second link 52b (the direction indicated by the arrow in the drawings is positive); and $F_C$: the force acting on the distal end of the second end effector finger 48b perpendicularly to the longitudinal direction of the second end effector finger 48b (the direction indicated by the arrow in the drawings is positive).

The torques and forces satisfy the following equations:

$$T_A = L_A F_A \tag{1}$$

$$T_B = L_B F_B = L_C F_C \tag{2}$$

Geometrically, the following equation is satisfied:

$$F_A = F_A \sin(\theta_d - \pi/2) \tag{3}$$

From the equations (1) through (3), the following equations are derived:

$$F_C = F_A (L_B/L_C)\{1/\sin(\theta_d - \pi/2)\} \tag{4}$$

$$T_B = T_A (L_B/L_A)\{1/\sin(\theta_d - \pi/2)\} \tag{5}$$

The distance $L_B$ between the first joint axis O1 and the third joint axis O3 and the angle $\theta_d$ formed between the link bar 36 and the second link 52b are determined according to the following equations based on the longitudinal length $L_A$ of the link bar 36, the longitudinal length $L_D$ of the first link 52a, and the angle $\theta_b$ formed between the first link 52a and the link bar 36:

$$L_B^2 = L_A^2 + L_D^2 - 2L_A L_D \cos\theta_b \tag{6}$$

$$L_D^2 = L_B^2 + L_A^2 - 2L_A L_B \cos\theta_d \tag{7}$$

The angle $\theta_f$ formed between the first link 52a and the second link 52b can be determined by:

$$L_A^2 = L_B^2 + L_D^2 - 2L_B L_D \cos\theta_f \tag{8}$$

It can be understood from the equation (4) that a power boosting effect is produced if the distance $L_B$ between the first joint axis O1 and the third joint axis O3 is greater than the longitudinal length $L_C$ of the second end effector finger 48b. The equation (6) indicates that the distance $L_B$ between the first joint axis O1 and the third joint axis O3 is maximum when the angle $\theta_b$ formed between the first link 52a and the link bar 36 is maximum, i.e., when the first and second end effector fingers 48a, 48b are maximally closed on each other. Therefore, at least when the first and second end effector fingers 48a, 48b are maximally closed on each other, if the distance $L_B$ between the first joint axis O1 and the third joint axis O3 is greater than the longitudinal length $L_C$ of the second end effector finger 48b, the power boosting effect is recognized. According to the present embodiment, such a relationship is satisfied.

It can also be understood from the equation (5) that a power boosting effect is produced if the distance $L_B$ between the first joint axis O1 and the third joint axis O3 is greater than the longitudinal length $L_A$ of the link bar 36. The equation (6) indicates that the distance $L_B$ between the first joint axis O1 and the third joint axis O3 is maximum when the first and second end effector fingers 48a, 48b are maximally closed on each other. Therefore, at least when the first and second end effector fingers 48a, 48b are maximally closed on each other, if the distance $L_B$ between the first joint axis O1 and the third joint axis O3 is greater than the longitudinal length $L_A$ of the link bar 36, the power boosting effect is recognized. According to the present embodiment, such a relationship is satisfied.

It can further be understood from the equations (4) and (5) that if the angle $\theta_d$ formed between the link bar 36 and the second link 52b is not $\pi$, then a power boosting effect is produced. Since a power boosting effect should preferably be recognized when the first and second end effector fingers 48a, 48b are maximally closed on each other, the angle $\theta_d$ formed between the link bar 36 and the second link 52b should not preferably be $\pi$ when the first and second end effector fingers 48a, 48b are maximally closed on each other. In particular, it can be seen that the power boosting effect is extremely large if the angle $\theta_d$ formed between the link bar 36 and the second link 52b is in the vicinity of $\pi/2$. According to the present embodiment, therefore, when the first and second end effector fingers 48a, 48b are maximally closed on each other, the angle $\theta_d$ formed between the link bar 36 and the second link 52b should preferably be as close to $\pi/2$ as possible.

If the angle $\theta_d$ is not only in the vicinity of $\pi/2$, but also in the range from $\pi/3$ (60°) through $2\pi/3$ (120°), then the force $F_B$ acting on the distal end of the second link 52b is theoretically be not less than twice the force $F_A$ acting on the distal end of the link bar 36. Because the power boosting effect (toggle mechanism effect) is noticeably developed, the angle $\theta_d$ is in the range from $\pi/3$ (60°) through $2\pi/3$ (120°) according to the present embodiment.

If the same condition as described above is achieved not only when the first and second end effector fingers 48a, 48b are maximally closed on each other, but also when the first and second end effector fingers 48a, 48b are maximally opened away from each other, a power boosting effect (toggle mechanism effect) is obtained by the same link angle. For peeling off a living body tissue with the manipulator 16, the manipulator 16 is required to apply a force (referred to as a peeling force) when the first and second end effector fingers 48a, 48b are opened away from each other. When the first and second end effector fingers 48a, 48b are maximally opened away from each other as shown in FIG. 6C, the angle $\theta_d$ is also in the range from $\pi/3$ (60°) through $2\pi/3$ (120°), producing a large peeling force.

The first end effector 24a and the second end effector 24b may be arranged so as to cross each other at the first junction 54a. According to such a modification, first end effector 24a and the second end effector 24b are opened and closed in reverse directions with respect to the direction in which the link bar 36 rotates.

The second link 52b and the link bar 36 may not necessarily turn across the plane formed by the longitudinal axis of the first link 52a and the first joint axis O1.

Operation of the manipulator 16 according to the first embodiment will be described below.

For closing a tubular tissue having opposite ends fixed, such as an artery, a collateral thereof, or the like with a clip using the manipulator 16, a clip is placed between the first and second end effector fingers 48a, 48b. The operator holds and operates the operating unit 22 to insert the working unit 18 into the body cavity and move the working unit 18 to the tubular tissue. The operator then turns the first and second end effectors 24a, 24b about the yaw axis and the pitch axis to bring the clip into an optimum posture.

Then, the operator opens and closes the first and second end effector fingers 48a, 48b about the gripper axis, and crimps the clip to close the tubular tissue. At this time, if it is necessary to prevent the first and second end effectors 24a, 24b from being moved carelessly, then the motors of the manipulator 16 are de-energized not to turn the first and second end effectors 24a, 24b about the yaw axis and the pitch axis. When the first and second end effector fingers 48a, 48b are opened and closed about the gripper axis, the first end effector 24a is not theoretically offset with respect to the second end effector 24b. The link bar 36 and the second link 52b is turned from one side to the other side of the gripping reference plane, sufficiently opening the second end effector finger 48b widely away from the first end effector finger 48a. The slide pin 56 on the distal end of the link bar 36 is brought into abutment against the proximal ends of the slots 60 to prevent the second end effector finger 48b from being opened unduly away from the first end effector finger 48a, so that the clip is prevented from falling off.

When the first and second end effector fingers 48a, 48b are maximally closed on each other, the distance $L_B$ between the first joint axis O1 and the third joint axis O3 becomes greater than the longitudinal length $L_C$ of the second end effector finger 48b, the distance $L_B$ between the first joint axis O1 and the third joint axis O3 becomes greater than the longitudinal length $L_A$ of the link bar 36, and the angle $\theta_d$ formed between the link bar 36 and the second link 52b is in the vicinity of $\pi/2$. Therefore, a power boosting effect is fully produced to crimp the clip with sufficient gripping forces.

The manipulator 16 according to the first embodiment offers the following advantages. The first end effector 24a, the second end effector 24b, and the link bar 36 jointly make up a power boosting mechanism for increasing the gripping forces produced by the first end effector finger 48a and the second end effector finger 48b. When the first and second end effector fingers 48a, 48b are opened and closed, the first end effector 24a is not theoretically offset with respect to the second end effector 24b. Accordingly, the operator finds it easy to position the working unit 18 with respect to a living body tissue to be treated and to apply a clip to the living body tissue. The operator thus can operate the manipulator 16 neatly and smoothly.

When the first and second end effector fingers 48a, 48b are maximally closed on each other, the angle formed between the direction from the third joint axis O3 to the first joint axis O1 and the direction from the third joint axis O3 to the second joint axis O2 is in the range from $\pi/3$ (60°) through $2\pi/3$ (120°), resulting in a sufficient increase in the gripping forces.

The second link 52b and the link bar 36 are offset with respect to the first link 52a, and move across the gripping reference plane. Consequently, it is possible to open the second end effector finger 48b sufficiently widely from the first end effector finger 48a.

In addition, when the second link 52b and the link bar 36 are angularly moved relatively to each other while the distal end of the link bar 36 at the proximal end portion of the second link 52b is moving in the longitudinal direction of the second link 52b, the first and second end effector fingers 48a, 48b are opened and closed about the gripper axis. Since the distal end of the link bar 36 is moved with respect to the second link 52b in a limited range or since the second end effector finger 48b abuts against the first end effector finger 48a, the maximum open angle and the maximum closed angle between the first and second end effector fingers 48a, 48b are limited. In other words, the drive mechanism additionally has a function as a mechanical stopper to make the working unit simpler and smaller in size. With the mechanical stopper according to the present embodiment, the slide pin 56 is brought into abutment against the proximal ends of the slots 60 to limit the angular movement of the second link 52b and the link bar 36. Specifically, the second link 52b and the slide pin 56 abut against each other at a position sufficiently spaced from the first joint axis O1 about which the second link 52b is angularly movable. Accordingly, a smaller force is posed on the mechanical stopper under a given torque than if the second link 52b and the slide pin 56 abut against each other at a position closer to the first joint axis O1, so that the required mechanical strength of the mechanical stopper is relatively small. Since the maximum open angle between the first and second end effector fingers 48a, 48b is limited, the manipulator 16 is effective to prevent the clip from falling off and is capable of applying and crimping the clip smoothly.

According to the present embodiment, when the first end effector finger 48a and the second end effector finger 48b are opened away from and closed on each other, the first and second end effectors 24a, 24b are not turned about the yaw axis and the pitch axis. Therefore, when the manipulator 16 applies and crimps the clip, the first and second end effectors 24a, 24b are prevented from moving undesirably, allowing the operator to apply and crimp the clip reliably using the manipulator 16.

2nd Embodiment

Figure 8:
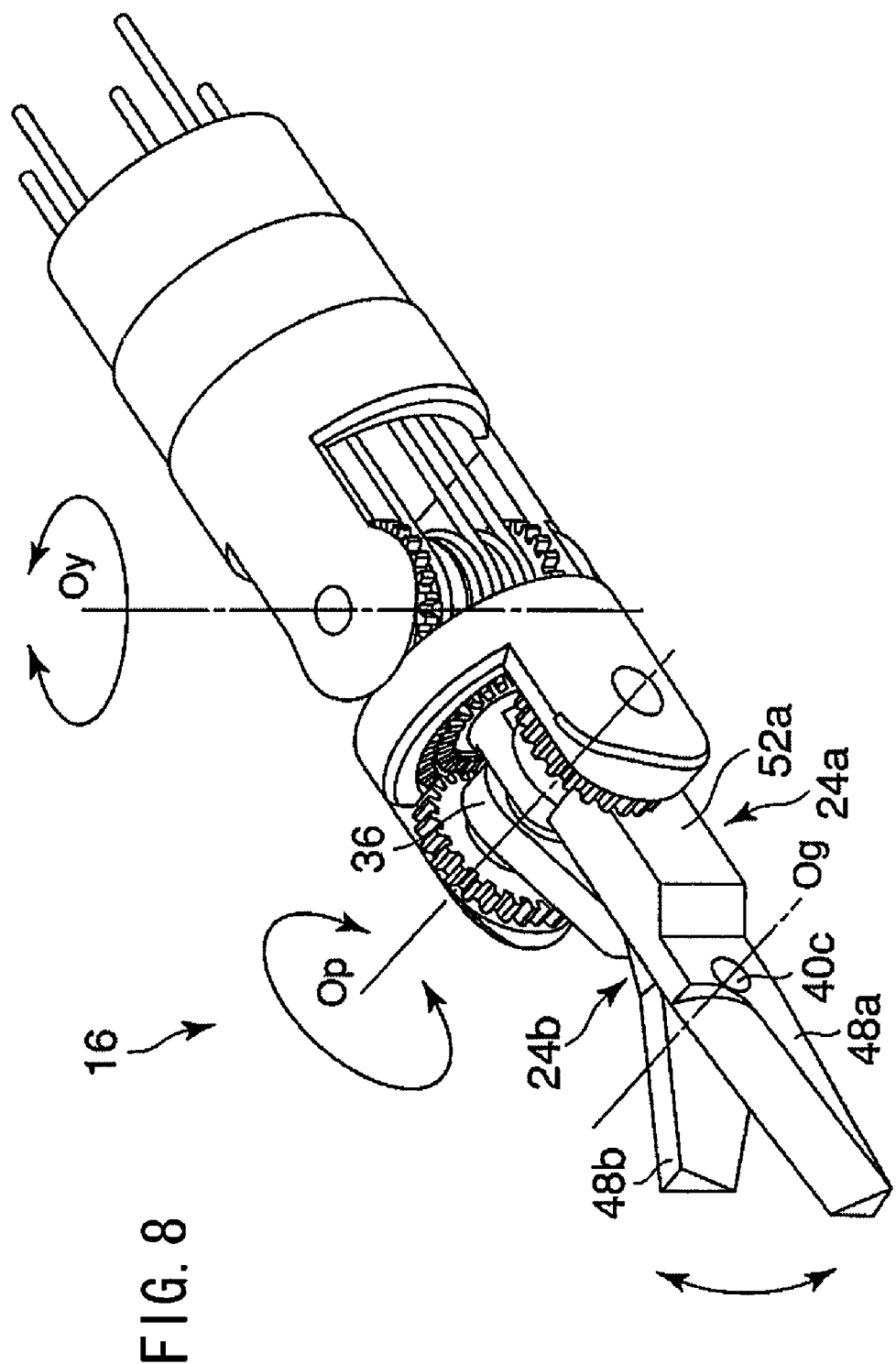
FIG. 8 is a perspective view of a working unit of a manipulator according to a second embodiment of the present invention.
Figure 9A:
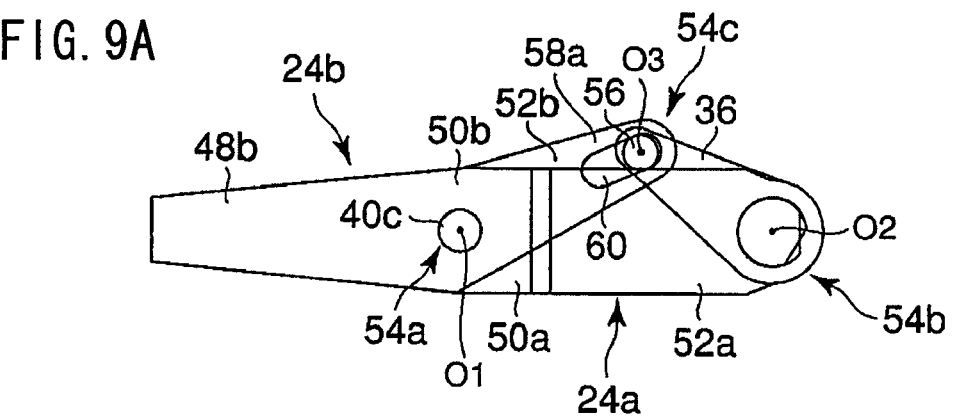
FIG. 9A is a side elevational view of the working unit of the manipulator according to the second embodiment of the present invention, the view showing a state in which the first and second end effectors of the working unit are maximally closed on each other.
Figure 9B:
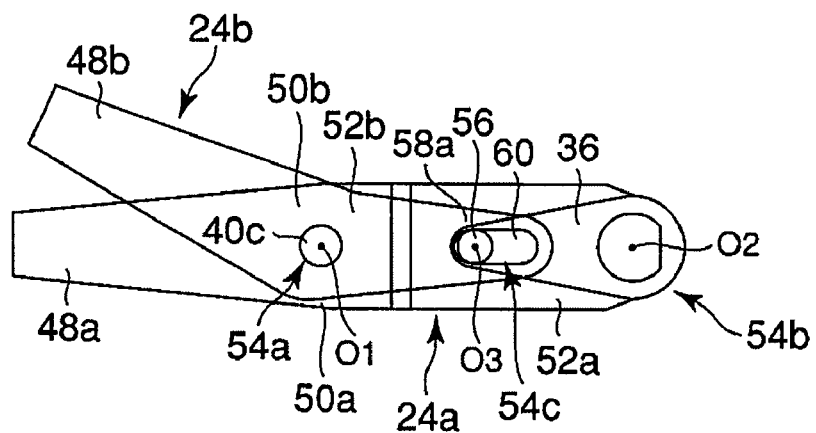
FIG. 9B is a side elevational view of the working unit of the manipulator according to the second embodiment of the present invention, the view showing a state in which the first and second end effectors of the working unit are in an intermediate position in their opening and closing operation.
Figure 9C:
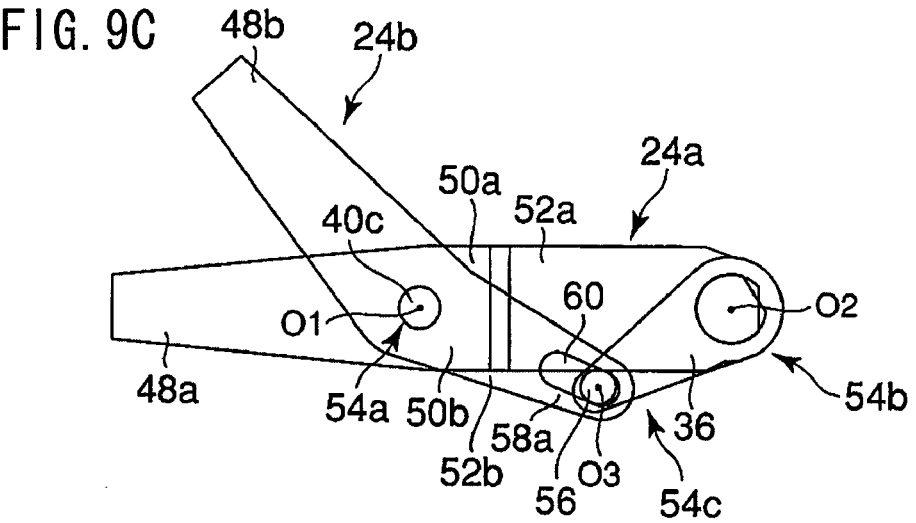
FIG. 9C is a side elevational view of the working unit of the manipulator according to the second embodiment of the present invention, the view showing a state in which the first and second end effectors of the working unit are maximally opened away from each other.

FIGS. 8 through 9C show a manipulator 16 according to a second embodiment of the present invention. Those parts of the manipulator 16 according to the second embodiment which are structurally and functionally identical to those of the manipulator 16 according to the first embodiment are denoted by identical reference characters, and will not be described in detail below.

The manipulator 16 according to the second embodiment serves as scissors, and has first and second end effector fingers 48a, 48b in the form of respective cutting blades.

In a process of manufacturing scissors, it is important to perform mutual lapping on the cutting blades to provide sharp cutting edges. According to the second embodiment, mutual lapping is performed on first and second end effector fingers 48a, 48b in assembling the first end effector 24a, the second end effector 24b, and the third turn shaft 40c. Specifically, mutual lapping can easily be performed on first and second end effector fingers 48a, 48b without the intervention by the pulleys and the gears for actuating the first and second end effectors 24a, 24b. After mutual lapping has been performed on first and second end effector fingers 48a, 48b, the first end effector 24a, the second end effector 24b, and the third turn shaft 40c are finally assembled. Therefore, the efficiency with which the first end effector 24a, the second end effector 24b, and the third turn shaft 40c are assembled together is higher than if they are assembled while mutual lapping is being performed on first and second end effector fingers 48a, 48b.

The mechanical stopper provided by the third junction 54c limits the maximum closed angle between the first and second end effector fingers 48a, 48b. If the maximum closed angle between the first and second end effector fingers 48a, 48b is not limited, then utmost care should be paid not to close the first and second end effector fingers 48a, 48b excessively on each other. However, the mechanical stopper according to the present embodiment requires no such care, allowing the manipulator 16 to be operated neatly and smoothly.

FIGS. 10 through 13C show a manipulator 16 according to a third embodiment of the present invention. Those parts of the manipulator 16 according to the third embodiment which are structurally and functionally identical to those of the manipulator 16 according to the first embodiment are denoted by identical reference characters, and will not be described in detail below.

The manipulator 16 according to the third embodiment serves as a needle driver for gripping a curved needle when it sutures a living body tissue.

Figure 10:
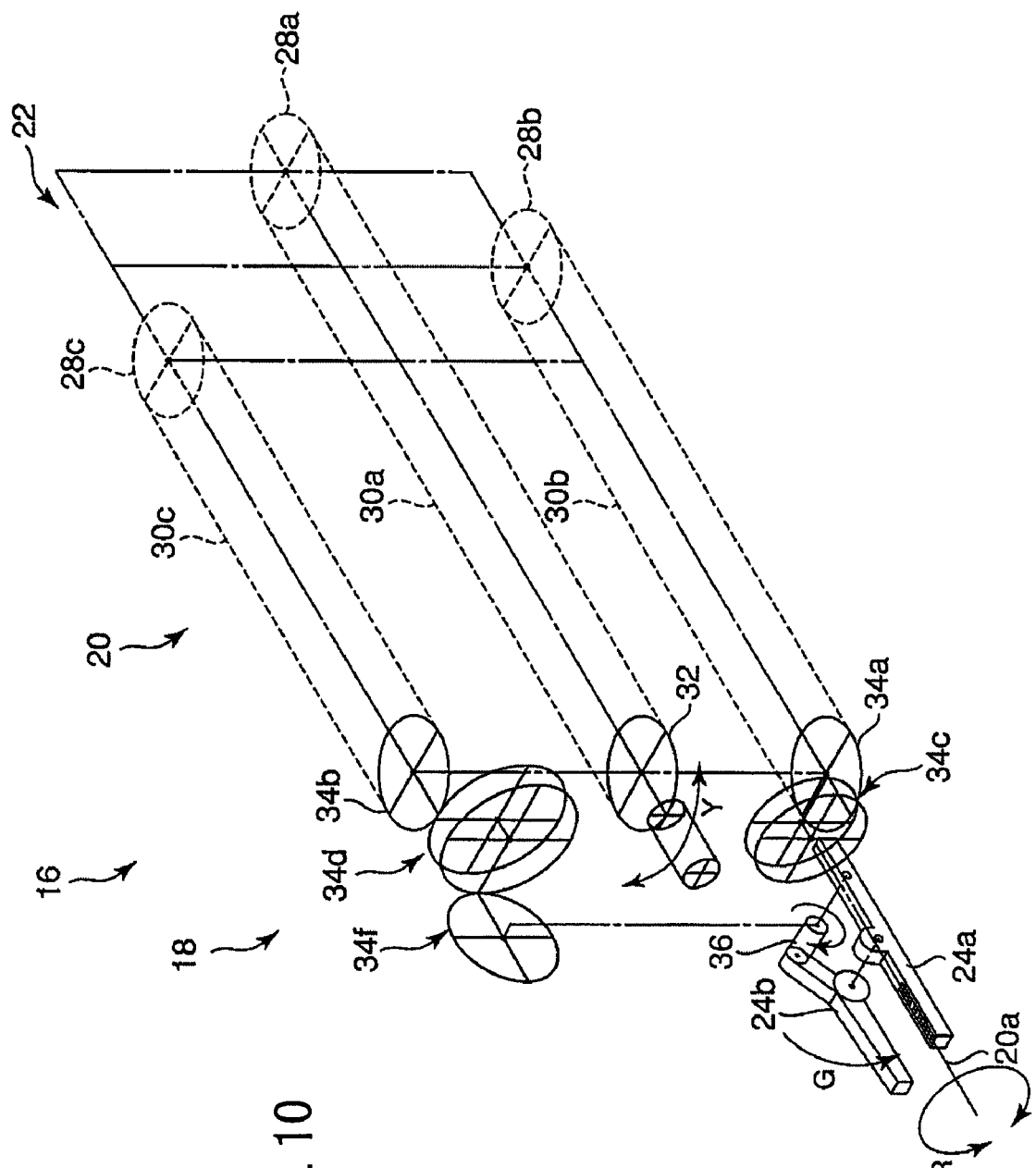
FIG. 10 is a schematic perspective view of a drive mechanism of a manipulator according to a third embodiment of the present invention.
Figure 11:
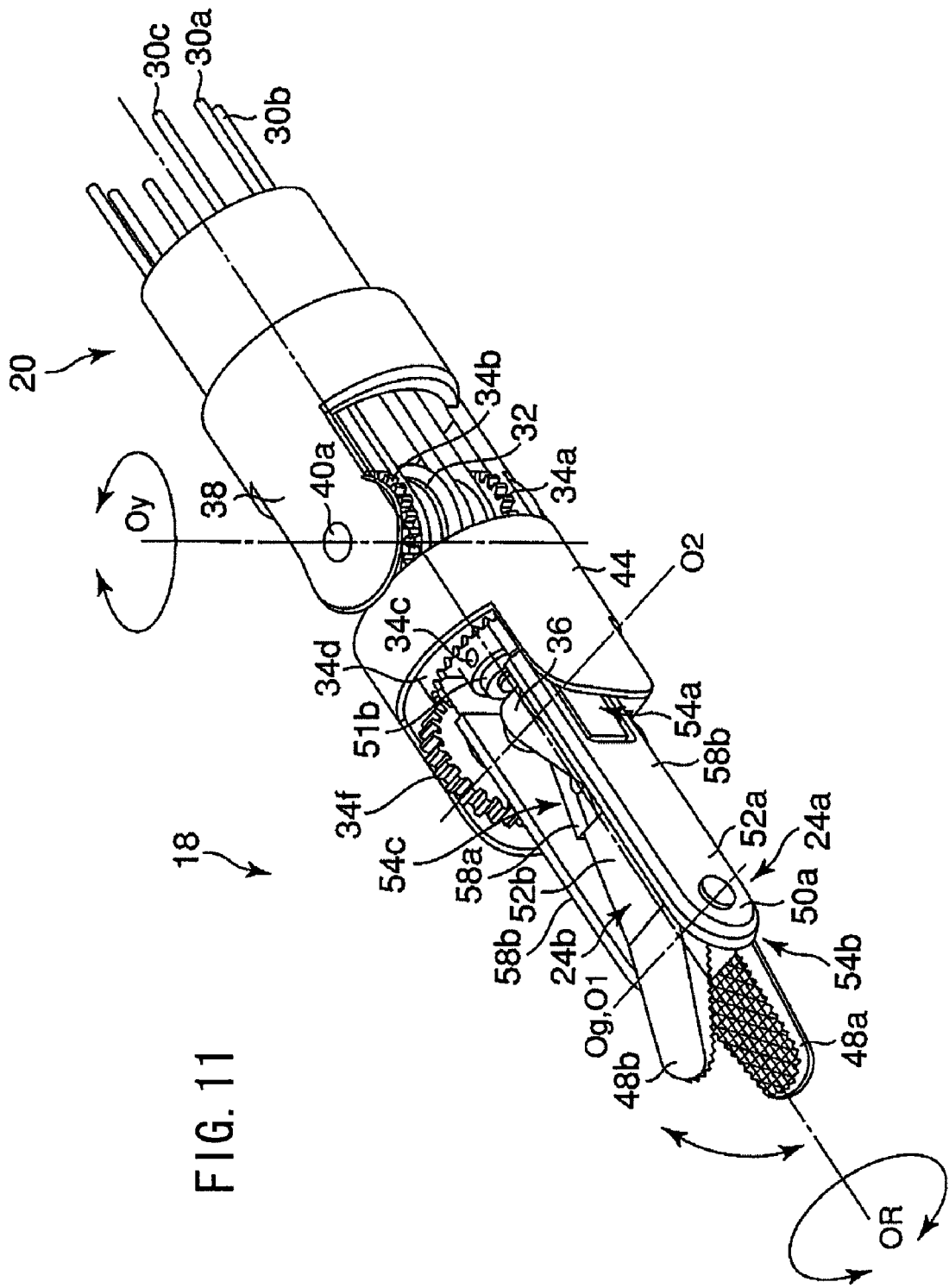
FIG. 11 is a perspective view of a working unit of the manipulator according to the third embodiment of the present invention.
Figure 12:
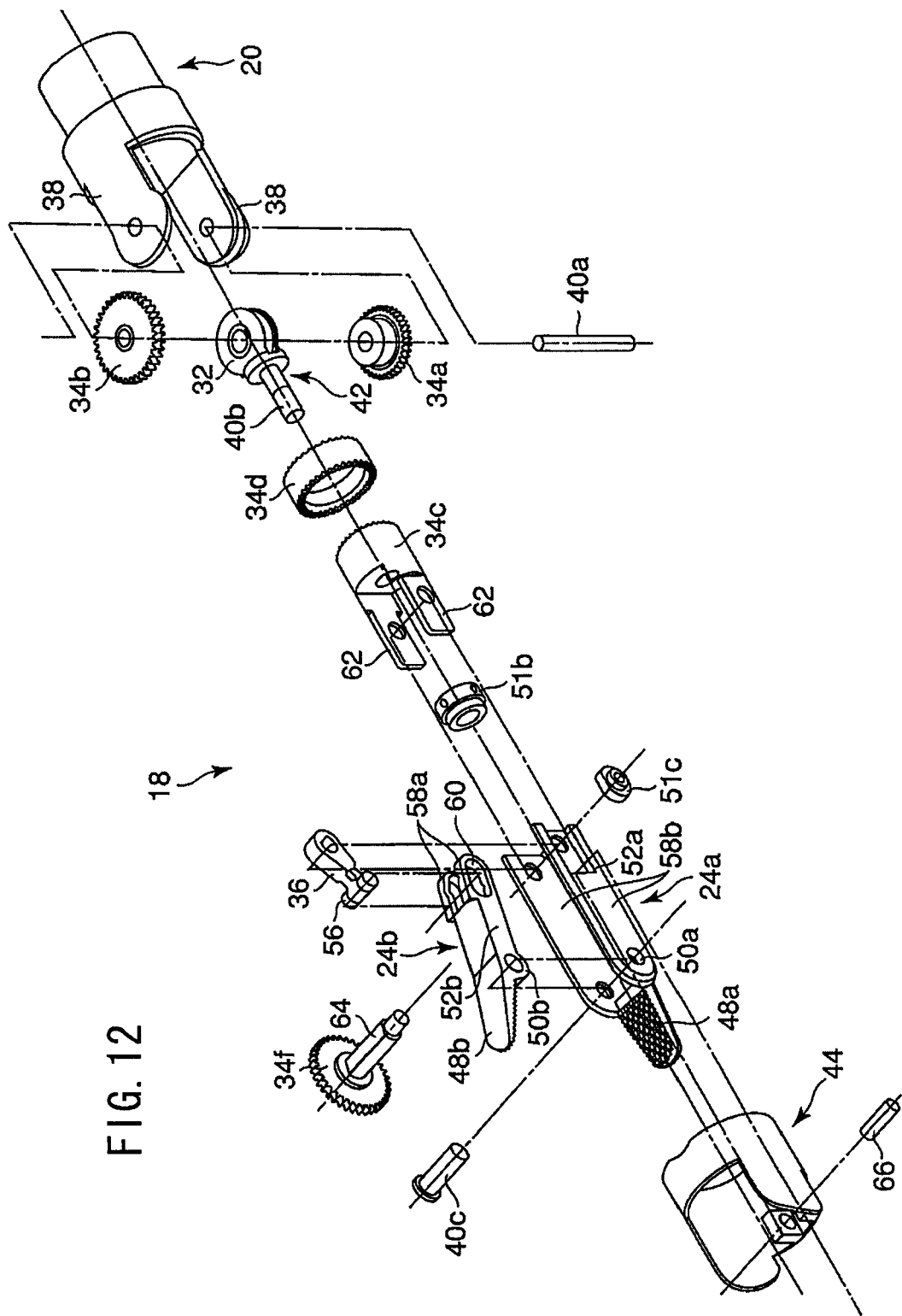
FIG. 12 is an exploded perspective view of the working unit of the manipulator according to the third embodiment of the present invention.
Figure 13A:
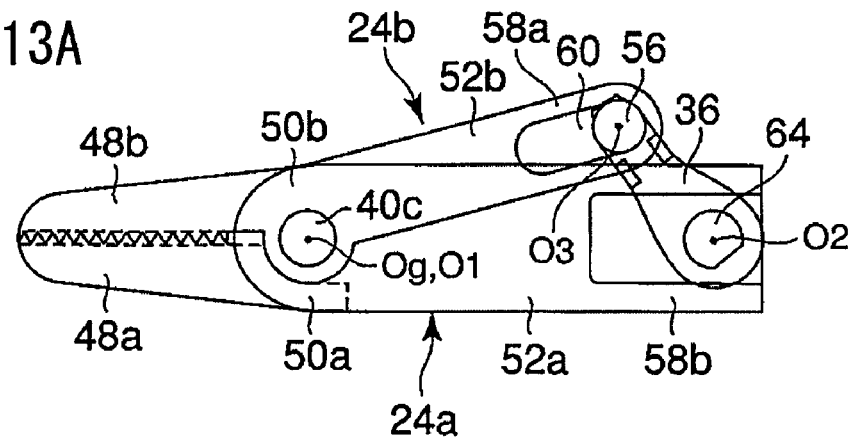
FIG. 13A is a side elevational view of the working unit of the manipulator according to the third embodiment of the present invention, the view showing a state in which first and second end effectors of the working unit are maximally closed on each other.
Figure 13B:
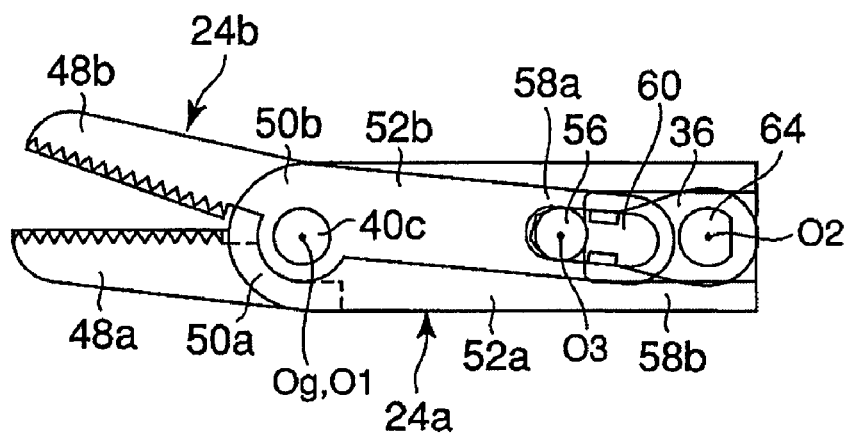
FIG. 13B is a side elevational view of the working unit of the manipulator according to the third embodiment of the present invention, the view showing a state in which the first and second end effectors of the working unit are in an intermediate position in their opening and closing operation.
Figure 13C:
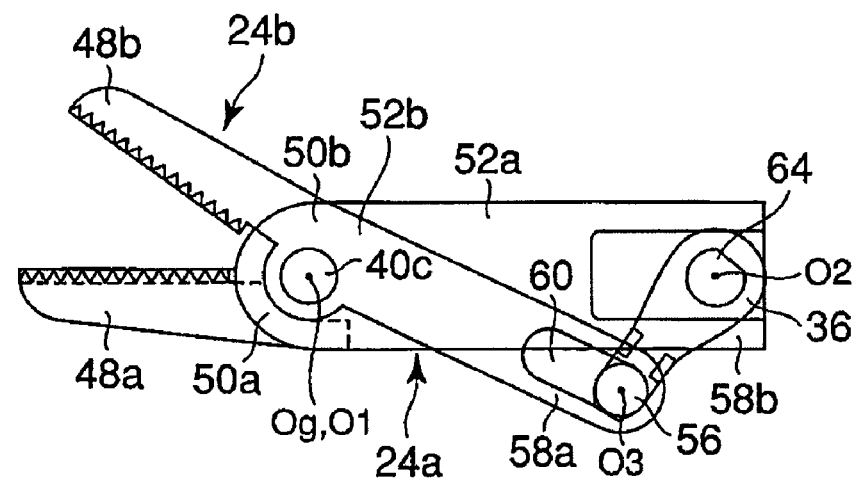
FIG. 13C is a side elevational view of the working unit of the manipulator according to the third embodiment of the present invention, the view showing a state in which the first and second end effectors of the working unit are maximally opened away from each other.

As shown in FIG. 10, the first and second end effectors 24a, 24b according to the third embodiment are angularly movable about a roll axis which is essentially in alignment with the main axis 20a of the working unit 18, in the directions indicated by the arrow R, rather than about the pitch axis. A torque for angularly moving the first and second end effectors 24a, 24b about the roll axis is transmitted from the second motor output shaft 28b through the second wire 30b and the first and third gears 34a, 34c to the first and second end effectors 24a, 24b.

As shown in FIGS. 11 through 13C, the working unit 18 has the first turn shaft 40a, the pulley 32 of the main shaft 42, and the first and second gears 34a, 34b as with the first embodiment. The distal end portion of the main shaft 42 serves as the second turn shaft 40b extending along the axis of the main shaft 42. The third gear 34c has a hollow cylindrical portion on its proximal end which is rotatably fitted over the second turn shaft 40b for rotation about the axis of the second turn shaft 40b. A first fastening nut 51b is threaded over the distal end of the second turn shaft 40b for preventing the third gear 34c from being axially displaced with respect to the second turn shaft 40b.

The hollow cylindrical portion of the third gear 43c has a toothed proximal end face having a number of successive gear teeth on an entire circumferential surface thereof. The gear teeth of third gear 43c are held in mesh with the gear teeth of the first gear 34a, so that the third gear 34c can be rotated by the first gear 34a. The hollow cylindrical portion of the third gear 43c has a pair of diametrically opposite legs 62 projecting toward the distal end thereof and spaced from each other in a direction substantially perpendicular to the first and second turn shafts 40a, 40b. The first link 52a of the first end effector 24a has a pair of fork ends 58a facing each other extending in the longitudinal direction of the first link 52a. The fork ends 58a have respective fitting grooves defined in their proximal end portions and extending in the longitudinal direction of the first link 52a. The legs 62 have respective distal end portions fitted in the respective fitting grooves.

When the first gear 34a is rotated by the second wire 30b, the third gear 34c is rotated to angularly move the first end effector 24a, together with the second end effector 24b, around the second turn shaft 40b, i.e., the roll axis Oy.

The fourth gear 34d, which is of a ring shape, is rotatably mounted on the second turn shaft 40b of the main shaft 42 for rotation about the axis of the second turn shaft 40b. The fourth gear 34d has toothed distal and proximal end faces each having a number of successive gear teeth on an entire circumferential surface thereof. The gear teeth on the proximal end face of the fourth gear 34d are held in mesh with the gear teeth of the second gear 34b, so that the fourth gear 34d can be rotated by the second gear 34b. The legs 62 of the third gear 34c and the fork ends 58b of the first end effector 24a have respective insertion holes defined therethrough in a direction substantially perpendicular to the first and second turn shafts 40a, 40b. A coupling pin 64 that is rotatable about its own axis is inserted in these insertion holes. The sixth gear 34f, which is substantially disk-shaped, is substantially coaxially connected to an end of the coupling pin 64, and has a number of successive gear teeth on an entire outer circumferential surface thereof. The gear teeth of the sixth gear 34f are held in mesh with the gear teeth on the distal end face of the fourth gear 34d, so that the sixth gear 34f can be rotated by the fourth gear 34d. A second fastening nut 51c is threaded over the other end of the coupling pin 64. The sixth gear 34f and the second fastening nut 51c prevent the coupling pin 64 from being axially displaced with respect to the legs 62 and the fork ends 58b.

The second link 52b of the second end effector 24b and the link bar 36 are disposed between the fork ends 58b of the first link 52a of the first end effector 24a. Between the fork ends 58b, the coupling pin 64 has an asymmetric cross-sectional shape perpendicular to the axis thereof, and is nonrotatably inserted in an engagement hole defined in the proximal end of the link bar 36. When the second gear 34b is rotated by the third wire 30c, the fourth and sixth gears 34d, 34f and the coupling pin 64 are rotated to angularly move the link bar 36 around the coupling pin 64. The first and second end effectors 24a, 24b, and the mechanism for opening and closing the first and second end effector fingers 48a, 48b about the gripper axis are identical to those according to the first embodiment except that the second link 52b and the link bar 36 are angularly movable between the fork ends 58b of the first link 52a, and will not be described in detail below (see FIGS. 13A through 13C). The first and second end effector fingers 48a, 48b have respective gripping surfaces machined (e.g., knurled) to prevent slippage for securely gripping a curved needle therebetween.

The fourth and sixth gears 34d, 34f are covered with the cover 44, and the cover 44 and the proximal end of the first end effector 24a are fixed to each other by a fastening pin 66. The cover 44 is shaped so as not to obstruct the angular movement of the first and second end effectors 24a, 24b about the yaw axis and the opening and closing movement of the first and second end effectors 24a, 24b about the gripper axis and so as to allow the first and second end effectors 24a, 24b to rotate about the roll axis.

Operation of the manipulator 16 according to the third embodiment will be described below. For suturing a living body tissue with the manipulator 16, a suture is wound around the distal end portion of the connecting shaft 20 or the first and second end effectors 24a, 24b, and a curved needle to which an end of the suture is connected is gripped by the first and second end effector fingers 48a, 48b. Then, the first and second end effectors 24a, 24b are positioned near a living body tissue to be treated, and are turned about the yaw axis to bring themselves into an optimum posture for suturing the living body tissue. Then, the first and second end effectors 24a, 24b are turned about the roll axis to insert the curved needle into the living body tissue, and remove the curved needle from the living body tissue to suture the living body tissue to be treated. If necessary, the suture wound around the distal end portion of the connecting shaft 20 or the first and second end effectors 24a, 24b is released while one end of the suture is pinched by the first and second effector fingers 48a, 48b so as to intertwine the suture into a knot, thereby ligating the living body tissue.

The manipulator 16 according to the third embodiment offers the following advantages:

The second link 52b of the second end effector 24b and the link bar 36 are angularly movable between the fork ends 58b of the first link 52a of the first end effector 24a. Therefore, the second link 52b and the link bar 36 are angularly movable across the gripping reference plane. Consequently, it is possible to open the first and second end effector fingers 48a, 48b sufficiently widely from each other.

Since the second link 52b and the link bar 36 are angularly moved between the fork ends 58b, the distal end portion of the working unit 18 is of a shape which is relatively free of rough protrusions and surface irregularities. Accordingly, when the suture wound around the distal end portion of the connecting shaft 20 or the first and second end effectors 24a, 24b is removed to form a knot, the suture is less liable to be caught by or trapped in the working unit 18, so that the living body tissue can be ligated more smoothly.

In each of the above embodiments, the integral manipulator wherein the operating unit and the working unit are integrally combined with each other has been described. However, the working unit according to the present invention is also applicable to an articulated-arm manipulator for remotely controlling an articulated arm which has a working unit on its distal end. For example, if the end effectors of such an articulated-arm manipulator are to be offset with respect to each other, then it is necessary to incorporate an offset action into a processing sequence for setting a target position for the end effectors. However, the working unit according to the present invention dispenses with such a requirement.

Although certain preferred embodiments of the present invention have been shown and described in detail, it should be understood that various changes and modifications may be made therein without departing from the scope of the appended claims.

What is claimed is:

1. A manipulator comprising:
 a first end effector extending from its first end to its second end, said first end effector having a first end effector portion on said first end, which is at a distal end side of the manipulator, a first link on said second end, and a first joint disposed between said first end effector portion and said first link;
 a second end effector extending from its first end to its second end, said second end effector having a second end effector portion on said first end, which is at the distal end side of the manipulator, a second link on said second end, and a second joint disposed between said second end effector portion and said second link;
 a link bar extending from its first end to its second end;
 a first junction directly connecting said second joint to said first joint such that said second end effector has a longitudinal direction substantially perpendicular to a first joint axis which extends through said first junction substantially perpendicularly to a longitudinal direction of said first end effector, and said second end effector is angularly movable about said first joint axis with respect to said first end effector;
 a second junction directly connecting the second end of said link bar to a second end of said first link such that said link bar has a longitudinal direction substantially perpendicular to a second joint axis which extends through the second end of said first link substantially perpendicularly to a longitudinal direction of said first link, and said link bar is angularly movable about said second joint axis with respect to said first link; and
 a third junction connecting the first end of said link bar to a second end of said second link such that said second link has a longitudinal direction substantially perpendicular to a third joint axis which extends through the first end of said link bar substantially perpendicularly to said longitudinal direction of said link bar, said link bar is angularly movable about said third joint axis with respect to said second link, and the first end of said link bar is movable in the longitudinal direction of said second link with respect to said second link, wherein the first joint axis is the distal most joint axis and the second joint axis is the proximal most joint axis.

2. A manipulator according to claim 1, wherein when said first end effector portion and said second end effector portion are maximally closed on each other, an angle formed between a direction from said third joint axis to said first joint axis and a direction from said third joint axis to said second joint axis is in a range from $\lambda/3$ to $2\pi/3$.

3. A manipulator according to claim 1, wherein said second link and said link bar are angularly movable across a plane formed by the longitudinal direction of said first link and the direction of said first joint axis.

4. A manipulator according to claim 3, wherein said second link and said link bar are offset in the direction of said first and second joint axes with respect to said first link.

5. A manipulator according to claim 3, wherein said first link has a pair of portions extending in the longitudinal direction of said first link and disposed parallel to each other along said first joint axis, and said second link and said link bar are angularly movable between said pair of portions.

6. A manipulator according to claim 1, wherein said third junction has a mechanical stopper for limiting a range in which the first end of said link bar is movable with respect to said second link.

7. A manipulator according to claim 6, wherein said third junction has:

a slot defined in the second end of said second link and extending in the longitudinal direction of said second link; and a slide pin mounted on the first end of said link bar for sliding movement in said slot.

8. A manipulator according to claim 1, wherein said first and second end effector portions serve as cutting blades of scissors.

9. A manipulator according to claim 1, wherein said manipulator satisfies at least one of the conditions:

$$|1/\sin(\theta_d-\pi/2)|<L_B/L_A;$$

$$L_A<L_B;$$

$$|1/\sin(\theta_d-\pi/2)|<L_B/L_C;$$

$$L_C<L_B,$$

where $L_A$ represents the distance between the second joint axis and the third joint axis;

$L_B$ represents the distance between the first joint axis and the third joint axis;

$L_C$ represents the distance between the first joint axis and a distal end of said second end effector; and $\theta_d$ represents the angle formed between a direction from said third joint axis to said first joint axis and a direction from said third joint axis to said second joint axis.

* * * * *